United States Patent
Aksela et al.

(10) Patent No.: US 9,061,276 B2
(45) Date of Patent: Jun. 23, 2015

(54) CATALYST RECOVERY PROCESS

(75) Inventors: Reijo Aksela, Espoo (FI); Jussi Rissanen, Turku (FI)

(73) Assignee: KEMIRA OYJ, Helsinki (FI)

( * ) Notice: Subject to any disclaimer, the term of this patent is extended or adjusted under 35 U.S.C. 154(b) by 100 days.

(21) Appl. No.: 13/639,577

(22) PCT Filed: May 31, 2011

(86) PCT No.: PCT/FI2011/050506
§ 371 (c)(1),
(2), (4) Date: Dec. 11, 2012

(87) PCT Pub. No.: WO2011/151519
PCT Pub. Date: Dec. 8, 2011

(65) Prior Publication Data
US 2013/0190526 A1    Jul. 25, 2013

(30) Foreign Application Priority Data
Jun. 2, 2010  (FI) ..................... 20105620

(51) Int. Cl.
| | |
|---|---|
| *C07C 213/06* | (2006.01) |
| *B01J 38/68* | (2006.01) |
| *B01J 27/232* | (2006.01) |
| *B01J 27/28* | (2006.01) |
| *C07C 227/14* | (2006.01) |
| *B01J 23/10* | (2006.01) |

(52) U.S. Cl.
CPC . *B01J 38/68* (2013.01); *B01J 23/10* (2013.01); *B01J 27/232* (2013.01); *B01J 27/28* (2013.01); *C07C 227/14* (2013.01)

(58) Field of Classification Search
USPC .......................................... 560/171
See application file for complete search history.

(56) References Cited

U.S. PATENT DOCUMENTS 4,031,031 A    6/1977  Yamaguchi et al.

FOREIGN PATENT DOCUMENTS

| JP | 2003292469 A | 10/2003 | |
|---|---|---|---|
| WO | 9745396 A1 | 12/1997 | |
| WO | 9946234 A1 | 9/1999 | |
| WO | WO-99/46234 * | 9/1999 | ............ C07C 213/06 |

OTHER PUBLICATIONS van Westernen, et al., "The Synthesis of Polyhydroxycaroxylates, Part 6, N-Alkylation of Amino Compounds by a Michael-type Addition with Maleate," Recl. Tray. Chim. Pays-Bas, vol. 109, pp. 474-478.
International Search Report and Written Opinion dated Jan. 30, 2012.
Finnish Search Report for the Priority Application dated Feb. 3, 2011.
International Preliminary Report on Patentability dated Nov. 6, 2012.

* cited by examiner

*Primary Examiner* — Kamal Saeed
*Assistant Examiner* — Janet L Coppins
(74) *Attorney, Agent, or Firm* — Thomas Horstemeyer, LLP

(57) ABSTRACT

The present invention relates to a method for recovering lanthanoid catalyst from the preparation of aspartic acid diethoxy succinate comprising contacting a carbonate source with a solution containing lanthanoid ions derived from said preparation and a chelating agent different from aspartic acid diethoxy succinate to precipitate lanthanoid carbonate followed by separating the precipitated lanthanoid carbonate from the solution.

20 Claims, 2 Drawing Sheets

US 9,061,276 B2

CATALYST RECOVERY PROCESS

CROSS REFERENCE TO RELATED APPLICATION

This application is the 35 U.S.C. §371 national stage of PCT application entitled "Catalyst Recovery Process," having serial number PCT/FI2011/050506, filed on 31 May 2011, which claims priority to Finland Application No. 20105620, filing date Jun. 2, 2010, which is incorporated by reference in its entirety.

TECHNICAL FIELD

The present invention relates to a method for recovering lanthanoid catalyst from the reaction mixture after the synthesis of a chelating agent.

BACKGROUND OF THE INVENTION

WO 97/45396 discloses N-bis- and N-tris-[(1,2-dicarboxy-ethoxy)-ethyl]-amine derivatives including N-bis-[(1, 2-dicarboxy-ethoxy)-ethyl]-aspartic acid (also called aspartic acid diethoxy succinate or AES), and the use of these derivatives as chelating agents of metals. These derivatives can be prepared by reacting a di- or triethanolamine with an alkali metal or alkaline earth metal salt of maleic acid in the presence of a catalyst such as a lanthanide compound or an alkaline earth metal compound. This is a typical Michael addition reaction.

A method to prepare N-[2-(1,2-dicarboxyethoxy)-ethyl] aspartic acid (EDODS) by $La^{3+}$-catalyzed O-alkylation of maleic acid salts has been described by J. van Westrenen et al. in Recl. Tray. Chim. Pays-Bas., vol. 109, 1990, p. 474-478.

Various methods to separate lanthanum from product solutions have been described in the literature. For example the precipitation of lanthanum as oxalate has been described. Thus, the lanthanum(III) ion used as a catalyst can be separated from the oxalate precipitate by treating the precipitate with nitric acid or hydrochloric acid. Moreover, the lanthanum oxalate precipitate can after filtration be treated at high temperatures. At 400° C. the oxalate is calcined to form carbonate and at temperatures of about 800-900° C. lanthanum oxide is formed. Both products can be reused as catalysts.

Lanthanum is a known catalyst which may be used in the Michael addition wherein a hydroxyl group is typically O-alkylated by addition to maleate. Useful lanthanum(III) compounds are lanthanum maleate, lanthanum(III) nitrate, lanthanum(III) chloride, lanthanum oxide and lanthanum octanoate.

The aim of the present invention is to improve the recovery of lanthanum catalyst or other lantanoid catalysts from the preparation of aspartic acid diethoxy succinate.

SUMMARY OF THE INVENTION

According to the present invention it was surprisingly found that the separation of lanthanoid catalyst from the preparation of aspartic acid diethoxy succinate can be essentially improved by introducing another chelating agent, especially imino disuccinic acid (ISA) or ethylene diamine disuccinic acid (EDDS).

DETAILED DESCRIPTION OF THE INVENTION

Figure 1:
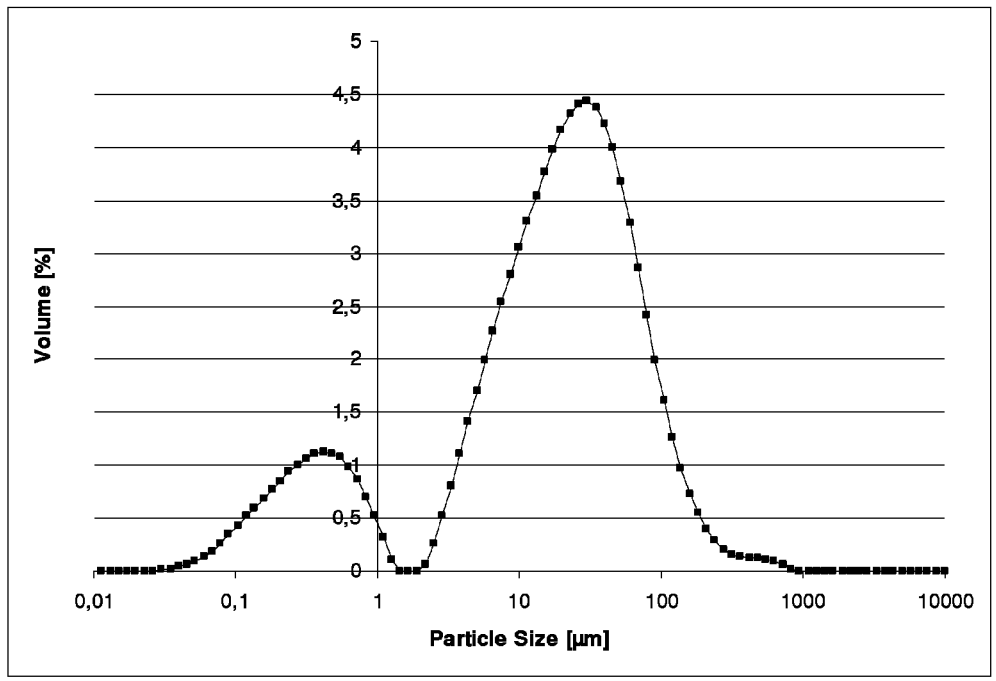
FIG. 1 shows the particle size distribution of lanthanum carbonate precipitate obtained according to conventional techniques.

In one aspect of the invention there is provided a method for recovering lanthanoid catalyst from the preparation of aspartic acid diethoxy succinate (AES) comprising contacting a carbonate source with a solution containing lanthanoid ions derived from said preparation and an additional chelating agent, i.e. a chelating agent different from aspartic acid diethoxy succinate, to precipitate lanthanoid carbonate followed by separating the precipitated lanthanoid carbonate from the solution.

The carbonate source is preferably an alkali metal carbonate or alkaline earth metal carbonate or carbon dioxide. The alkali metal is preferably sodium or potassium and the alkaline earth metal is preferably calcium or magnesium. A preferred carbonate source is sodium carbonate.

Preferred chelating agents are imino disuccinic acid (ISA) and ethylene diamine disuccinic acid (EDDS).

In one preferred embodiment of the invention the AES is prepared by reacting diethanol amine with maleate under alkaline conditions in the presence of the lanthanoid catalyst and a chelating agent comprising ISA which is formed in situ by adding aspartic acid into the reaction mixture where it reacts with unreacted maleate to form ISA.

In another preferred embodiment of the invention the AES is prepared by reacting diethanol amine with maleate under alkaline conditions in the presence of the lanthanoid catalyst and a chelating agent comprising EDDS which is formed in situ by adding ethylene diamine into the reaction mixture where it reacts with unreacted maleate to form EDDS.

In a second aspect of the invention there is provided a process for the preparation of aspartic acid diethoxy succinate (AES) comprising reacting diethanol amine with maleate under alkaline conditions in the presence of a lanthanoid catalyst to form aspartic acid diethoxy succinate. Said lanthanoid catalyst is precipitated from the reaction mixture by contacting the lanthanoid catalyst with a carbonate source and a chelating agent to form lanthanoid carbonate precipitate which is separated and reused as such as a lanthanoid catalyst in said process or converted into another lanthanoid catalyst to be used as a lanthanoid catalyst in said process. Said chelating agent is different from aspartic acid diethoxy succinate.

The separated lanthanoid carbonate precipitate can be converted into another salt such as lanthanoid(III) chloride or into lanthanoid(III) oxide.

The carbonate source is preferably an alkali metal carbonate or alkaline earth metal carbonate or carbon dioxide. The alkali metal is preferably sodium or potassium and the alkaline earth metal is preferably calcium or magnesium. A preferred carbonate source is sodium carbonate.

The AES, ISA and EDDS as well as the other chelating agents are preferably in the form of alkali metal salts or alkaline earth metal salts. Preferred alkali metal salts are sodium or potassium salts, and preferred alkaline earth metal salts are calcium or magnesium salts.

The lantanoid (previously named lanthanide) series comprises the fifteen elements with atomic numbers from 57 to 71. Preferred lanthanoid catalysts are lanthanum (La), praseodymium (Pr), neodymium (Nd), europium (Eu), dysprosium Dy), erbium (Er) and ytterbium (Yb).

An especially preferred lanthanoid catalyst is a lanthanum catalyst, and an especially preferred lanthanoid carbonate is lanthanum carbonate.

According to the invention the precipitated lanthanoid carbonate, preferably lanthanum carbonate, is preferably separated by filtration.

According to the invention the separated lanthanoid carbonate precipitate, preferably lanthanum carbonate precipitate, is preferably essentially free from particles having a particle size of less than 1 μm, preferably less than 2 μm. Essentially free means that less than 5%, preferably less than 3% by volume of the particles has a particle size of less than 1 μm, preferably less than 2 μm.

Preferred chelating agents which can be used in the present invention have following formula I, II or III.

A preferred chelating agent is a compound having following general formula

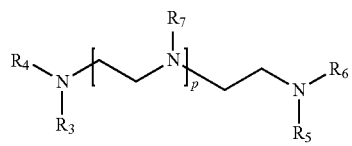

wherein p is 0 or an integer of 1 to 10, $R_3$, $R_4$, $R_5$, $R_6$ and $R_7$ are independently a hydrogen atom or an alkyl chain having 1 to 6 carbon atoms and containing one or more active chelating ligands, such as carboxylic, phosphonic or hydroxyl group(s) or a salt thereof.

The alkyl chain is preferably methylene —$CH_2$— or ethylene —$CH_2CH_2$—.

In formula I $R_3$, $R_4$, $R_6$ and $R_7$ preferably represent the same group.

Examples of chelating agents according to the above formula I are polyaminopolycarboxylic acids and polyaminopolymethylenephosphonic acids.

The polyaminopolycarboxylic acids can be produced by the conventional route from the polyamine and formaldehyde and sodium cyanide or hydrocyanic acid. The more suitable route for small scale production is to use a haloacetic acid, especially monochloroacetic acid as a reactant.

Preferred polyaminopolycarboxylic acids are:
DTPA: p=1, $R_3$=$R_4$=$R_5$=$R_6$=$R_7$=—$CH_2COOH$
TTHA: p=2, $R_3$=$R_4$=$R_5$=$R_6$=$R_7$=—$CH_2COOH$
EDTA: p=0, $R_3$=$R_4$=$R_5$=$R_6$=—$CH_2COOH$
HEDTA: p=0, $R_3$=$R_4$=$R_5$=—$CH_2COOH$, $R_5$=—$CH_2CH_2OH$
EDDS: p=0, $R_3$=$R_5$=H, $R_4$=$R_6$=—CH(COOH)$CH_2COOH$ (ethylenedi-aminedisuccinic acid)

The polyaminopolymethylenephosphonic acids are made conventionally from the corresponding polyamine, formaldehyde and phosphonic acid. With the higher amines a full substitution with acetic acid groups or methylenphosphonic acid groups will become more and more difficult. These chelating agents will also perform well in the composition but an incomplete substitution will make the chelating agents more prone for decomposition by hydrogen peroxide.

Preferred polyaminopolymethylenephosphonic acids are:
DTPMPA: p=1, $R_3$=$R_4$=$R_5$=$R_6$=$R_7$=—$CH_2POO_2H_2$
TTHMPA: p=2, $R_3$=$R_4$=$R_5$=$R_6$=$R_7$=—$CH_2POO_2H_2$
EDTMPA: p=0, $R_3$=$R_4$=$R_5$=$R_6$=—$CH_2POO_2H_2$ Another preferred chelating agent is a compound having following general formula

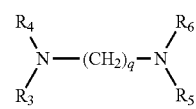

wherein q is an integer of 3 to 10, $R_3$, $R_4$, $R_5$ and $R_6$ are independently a hydrogen atom or an alkyl chain having 1 to 6 carbon atoms and containing one or more active chelating ligands, such as carboxylic, phosphonic or hydroxyl group(s) or a salt thereof.

The alkyl chain is preferably methylene —$CH_2$— or ethylene —$CH_2CH_2$—.

In formula II $R_3$, $R_4$ and $R_6$ preferably represent the same group.

Examples of chelating agents according to the above formula II are the commercially available hexamethylenediamine tetra(acetic acid) (q=6) and tetramethylenediamine tetra(methylenephosphonic acid) (q=4) having following formulae:

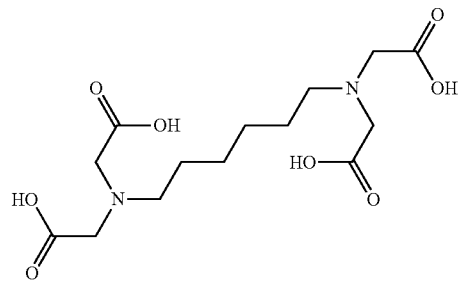 [SMILES: O=C(O)CN(CCCCCCN(CC(=O)O)CC(=O)O)CC(=O)O]

Hexamethylenediamine tetraacetic acid

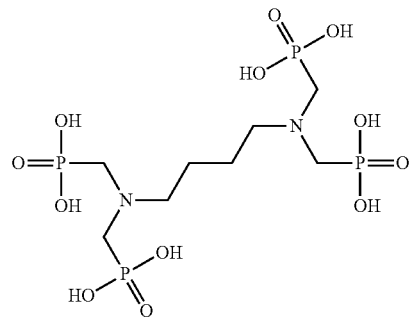 [SMILES: O=P(O)(O)CN(CCCCN(CP(=O)(O)O)CP(=O)(O)O)CP(=O)(O)O]

Tetramethylenediamine tetra(methylenephosphonic acid)

Yet another preferred chelating agent is a compound having following general formula:

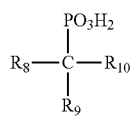

wherein
$R_8$ is a hydrogen atom, an alkyl group containing 1 to 6 carbon atoms or an alkyl chain having 1 to 6 carbon atoms and containing a carboxylic, phosphonic or hydroxyl group,
$R_9$ is a hydrogen atom, hydroxyl group, phosphonic group, carboxylic group or alkyl chain having 1 to 6 carbon atoms and containing one or two carboxylic groups, and
$R_{10}$ is a hydrogen atom, hydroxyl group, carboxylic group, alkyl group containing 1 to 6 carbon atoms or alkyl chain having 1 to 6 carbon atoms and containing a carboxylic group, or a salt thereof.

The alkyl chain is preferably methylene —$CH_2$— or ethylene —$CH_2CH_2$—.

An example of the non-nitrogen containing chelating agents according to the above formula III is 1-hydroxyethylidene-1,1-diphosphonic acid (HEDP).

A further preferred chelating agent is a compound having following general formula

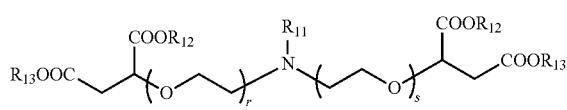

wherein $R_{11}$ is
a hydrogen atom
an alkyl chain containing 1-30 carbon atoms,
an alkyl chain containing 1-30 carbon atoms and 1-10 carboxylic acid groups attached to said chain, or alkali or alkaline earth metal salt thereof,
an alkyl chain containing 1-30 carbon atoms and 1-10 carboxylic acid esters attached to said chain,
a (poly)ethoxylated hydrocarbon chain containing 1-20 ethoxyl groups, or
a carboxylic acid amide containing 1-30 carbon atoms, where N—$R_{11}$ bond is an amide bond,
$R_{12}$ and $R_{13}$ are: hydrogen, an alkali metal ion or an alkaline earth metal ion or an alkyl group containing 1-30 carbon atoms,
r is 0 or 1, and
s is 0 or 1,
however, provided that the compound is not N-bis[2-(1,2-dicarboxy-ethoxy)-ethyl]-aspartic acid (AES) having following formula

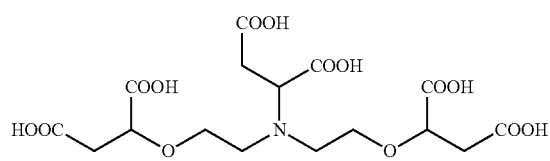 [SMILES: O=C(O)CC(OCCN(CCOC(CC(=O)O)C(=O)O)C(CC(=O)O)C(=O)O)C(=O)O]

Preferred N-bis- or tris-[(1,2-dicarboxy-ethoxy)ethyl]amines of formula IV are following

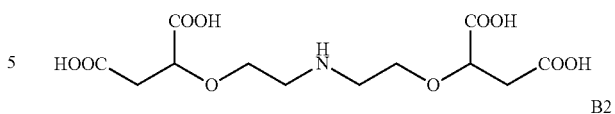
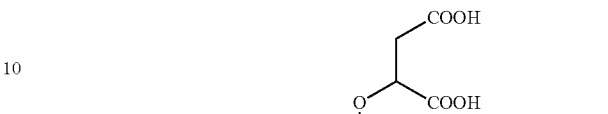
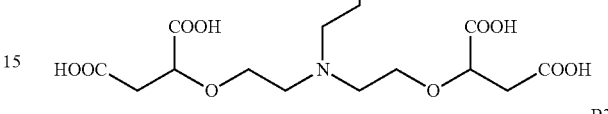

B1=N-bis[2-(1,2-dicarboxy-ethoxy)-ethyl]-amine
B2=N-tris[2-(1,2-dicarboxy-ethoxy)-ethyl]-amine
B3=N-[2-(1,2-dicarboxy-ethoxy)-ethyl]-(N-2-hydroxyethyl)aspartic acid A preferred N-bis-(1,2-dicarboxy-ethyl)amine of formula IV is iminodisuccinic acid (ISA) having following formula

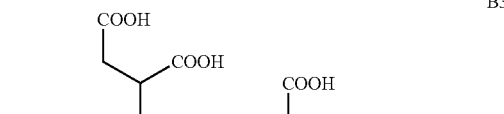

Though the formulas of the chelating agents are depicted above as acids, they are commercially normally sold as their alkali salts, mainly as their sodium salts and the formulas given above have to be understood as including both the free acids and their salts.

EXAMPLES

Reference Example 1

Precipitation of Lanthanum as Carbonate

1. Preparation of Aspartic Acid Diethoxy Succinate (AES) by Using a La Catalyst 73.61 g (0.751 moles) of maleic anhydride was dissolved in water using a magnetic stirrer and heating to about 70° C. The aqueous maleic acid solution was transferred into a three-neck flask in a preheated oil bath. $La_2(CO_3)_3$ (0.681 moles) was added as small lumps to the maleic acid solution. The addition was made slowly for controlling the effervescence caused by carbon dioxide. 30.92 g (0.250 moles) of diethanol amine (DEA) was added into the reaction mixture. After the addition of DEA the temperature of the mixture was raised to 90° C. 11.77 g of NaOH solution (aq. 48 wt %) was added to the reaction mixture, whereby the pH raised to 8.02. Generally the pH was adjusted, if necessary, in connection with the samplings by a NaOH solution (aq. 48 wt %). The aim was to raise the pH to about 9 after 12 hours from the start of the reaction. The first sample was taken immediately after the NaOH addition and the adjustment of the temperature.

The reaction was mixed and monitored at about 90° C. for 24 hours. The sampling interval was for the first four samples 4 hours and between samples 4 and 5 12 hours. Five samples were taken. More accurate information regarding the conditions and concentrations of the reaction mixture are set forth in following table 1.

TABLE 1

| Sample | Reaction time (hh:mm:ss) | AES (mole %) | pH | T ° C. |
|---|---|---|---|---|
| 1 | 0:00:00 | 1.05 | 8.02 | 90 |
| 2 | 4:00:00 | 30.55 | 9.12 | 92 |
| 3 | 8:00:00 | 52.69 | 9.64 | 93 |
| 4 | 12:00:00 | 55.79 | 9.50 | 93 |
| 5 | 24:00:00 | 58.29 | 9.68 | 93 |

2. Precipitation of Lanthanum Carbonate 431.80 g of the end product from the above synthesis was weighted into the starting flask. 166.82 g (0.472 moles) of $Na_2CO_3$ solution (aq. 30 wt %) was weighted into a precipitation vessel. The $Na_2CO_3$ concentration was about 2.5 times the concentration of lanthanum. The mixing was positioned close to the surface of the precipitation solution. The mixing was kept close to the liquid surface of the precipitation vessel during the whole precipitation, despite the elevation of the liquid surface. A motor pump fed the reaction solution to be precipitated into the precipitation vessel containing the carbonate solution. The feeding speed was about 7 g per minute. The carbonate solution vessel was surrounded by a heating water housing. The pH of the carbonate solution was 10.54 and the temperature 64° C. The rotation speed of the mixer was about 15 rpm. After the end of the precipitation, it was observed that the precipitate optionally had "encased" reaction solution in the precipitation vessel.

The precipitated reaction solution was filtrated by using a Büchner funnel, filter paper and suction. The obtained filtrate was a transparent solution. The filtrate was not rinsed. The remaining precipitate was subjected to a particle size analysis. The lanthanum content was determined from the filtrated reaction solution by XRF and ICP-AES devices. The particle size was measured by a particle size analyzer (Malvern Instruments, Mastersizer 2000, Hydro SM small volume sample dispersion unit). The results from the particle size measurements are shown in enclosed FIG. 1.

The results in FIG. 1 show that 15.94% (volume) of the particles have a size of below 2 μm and the vol. weighted mean diameter is 32.64 μm.

Reference Example 2

Precipitation of Lanthanum as Carbonate

1. Preparation of Aspartic Acid Diethoxy Succinate (AES) by Using a La Catalyst 98.18 g (1.001 moles) of maleic anhydride was dissolved in 354.80 g of water using a magnetic stirrer and heating to about 70° C. The aqueous maleic acid solution was transferred into a three-neck flask in a preheated oil bath. 0.244 moles of $La_2(CO_3)_3$ was added in small portions to the maleic acid solution. The addition was made slowly during about 5 minutes for controlling the effervescence caused by carbon dioxide. 30.80 g (0.249 moles) of diethanol amine (DEA) was added into the reaction mixture. After the addition of DEA the temperature of the mixture was raised to 90° C. 70.68 g (0.848 moles) of NaOH solution (aq. 48% by weight) was added to the mixture, whereby the pH raised to 8.03.

The reaction was mixed and monitored at about 90° C. for 24 hours. The sampling interval was for the first four samples 4 hours and between samples 4 and 5 12 hours. Five samples were taken. More accurate information regarding the conditions and concentrations of the reaction mixture are set forth in following table 2.

TABLE 2

| Sample | Reaction time (hh:mm:ss) | AES (mole %) | pH | T ° C. |
|---|---|---|---|---|
| 1 | 0:00:00 | 0.00 | 8.03 | 90 |
| 2 | 4:00:00 | 25.92 | 8.36 | 93 |
| 3 | 8:00:00 | 46.56 | 9.24 | 93 |
| 4 | 12:00:00 | 50.77 | 9.47 | 93 |
| 5 | 24:00:00 | 57.91 | 9.54 | 93 |

2. Precipitation of Lanthanum Carbonate 529.39 g of the end product from the above synthesis was weighted into the starting flask. 276.60 g (0.783 moles) of $Na_2CO_3$ solution (aq. 30 wt %) was weighted into a precipitation vessel. The mixing was positioned at the bottom of the precipitation vessel. The speed and position were adjusted during the precipitation if the precipitate formed in the precipitation vessel was observed to form encased solution. A motor pump fed the reaction solution to be precipitated into the precipitation vessel containing the carbonate solution. The feeding speed was about 7 g per minute. The carbonate solution vessel was surrounded by a heating water housing. The pH of the carbonate solution was 11.59 and the temperature 62° C. The rotation speed of the mixer was about 30 rpm. The mixing was continued after the end of the feeding of the solution for about 30 minutes whereafter the mixing and heating were stopped. The content of the precipitation vessel was allowed to settle until next day. A sample for particle size analysis of the precipitate was taken through the whole thickness of the solution-precipitate-phases from the bottom of the precipitation vessel up to the surface.

The precipitated reaction solution was filtrated by using a Büchner funnel, filter paper and suction. The obtained filtrate was a transparent solution. The lanthanum content was determined from the filtrated reaction solution by XRF and ICP-AES devices. The particle size was measured by a particle size analyzer (Malvern Instruments, Mastersizer 2000, Hydro SM small volume sample dispersion unit). The results from the particle size measurements are shown in enclosed FIG. 2

Figure 2:
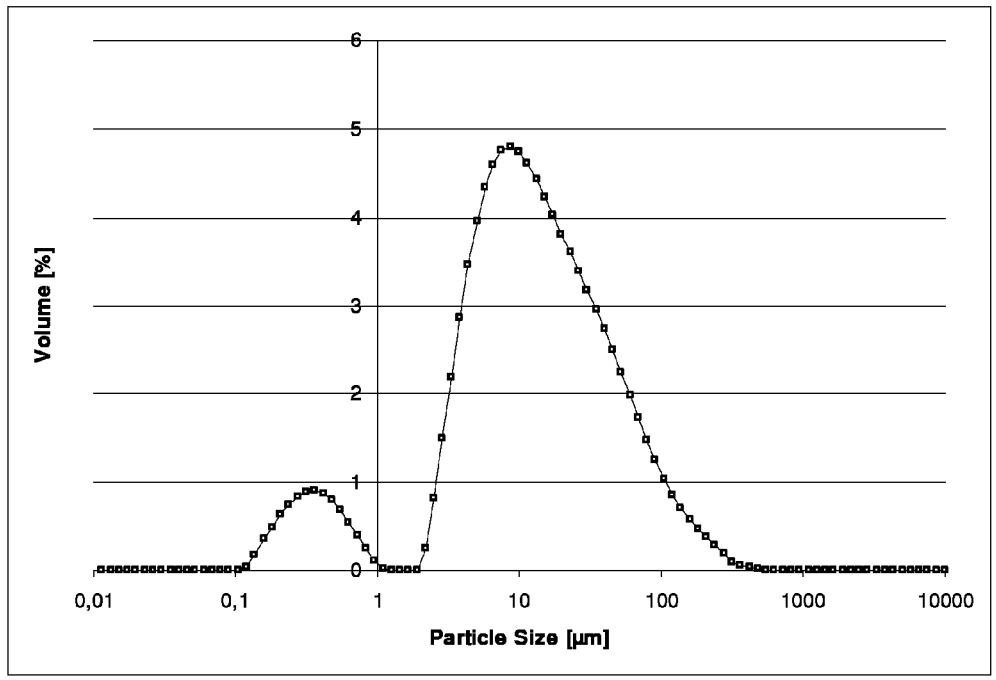
FIG. 2 shows the particle size distribution of lanthanum carbonate precipitate obtained according to conventional techniques.

The results in FIG. 2 show that 9.26% (volume) of the particles have a size of below 2 μm and the vol. weighted mean diameter is 20.26 μm. Example 2 shows that by controlling the precipitation, the amount of the small fraction (<2 μm) can be decreased.

Example 1

Precipitation of Lanthanum as Carbonate

1. Preparation of a Mixture of AES and EDDS 98.1 g (1.000 mole) of maleic anhydride was dissolved in 258.28 g of water using a magnetic stirrer and heating to about 70° C. The aqueous maleic acid solution was transferred into a three-neck flask in a preheated oil bath. 149.68 g (0.255 moles) of $La_2(CO_3)_3$ precipitate was added as an aqueous slurry to the maleic acid solution (T=70° C.). The addition was made slowly during about 5 minutes for controlling the effervescence caused by carbon dioxide. The pH before the addition of diethanol amine was 2.38 (T=73° C.). 30.96 g (0.252 moles) of diethanol amine was added into the reaction mixture. The addition of diethanol amine into the mixture raised the pH to 4.32 (T=76° C.). The temperature of the mixture was raised to about 90° C. The pH of the reaction solution was adjusted by adding 70.68 g (0.848 moles) of NaOH solution (aq. 48 wt %). The alkalinity of the reaction mixture was adjusted in connection with the second sample by adding 4.67 g (0.056 moles) of NaOH solution (aq. 48 wt %), whereby the pH raised to 8.64, and in connection with the third sample by adding 7.35 g (0.088 moles) of NaOH solution (aq. 48 wt %), whereby the pH raised to 9.05.

After about 12 hours from the start of the measurements 14.27 g (0.235 moles) of ethylene diamine was added. After the addition of ethylene diamine monitoring samples were taken with an interval of half an hour during six hours. Thereafter the sampling interval was extended. The reason for that was the fast synthesis of EDDS from ethylene diamine and maleate especially in the catalyzed reaction. At each occasion two samples were taken. Into one of the samples warm 30% by weight $Na_2CO_3$ solution was added immediately to stop the reaction catalyzed by lanthanum at the sampling moment. The other sample was stored and frozen. The analyses were performed on the samples treated with the carbonate solution. During the synthesis samples were taken at 23 moments. The total duration of the synthesis was 60 hours of which the 12 first were pure synthesis of AES.

More accurate information regarding the conditions and concentrations of the reaction mixture are set forth in following table 3.

TABLE 3

| Sample | Reaction time (hh:mm:ss) | EDDS (mole %) | AES (mole %) | Maleic acid (%) | pH | T ° C. |
|---|---|---|---|---|---|---|
| 1 | 0:00:00 | | 2.76 | 100.00 | 8.04 | 96 |
| 2 | 4:00:00 | | 4.89 | 90.43 | 7.97 | 90 |
| 3 | 8:00:00 | | 10.90 | 84.03 | 8.30 | 91 |
| 4 | 12:00:00 | | 37.90 | 57.36 | 9.25 | 90 |
| 5 | 12:15:00 | 0.00 | 38.68 | 59.59 | 10.33 | 85 |
| 6 | 12:55:00 | 10.38 | 41.00 | 46.71 | 10.32 | 93 |
| 7 | 13:30:00 | | 40.78 | 39.12 | 10.57 | 92 |
| 8 | 14:00:00 | 35.89 | 40.83 | 34.40 | 10.62 | 92 |
| 9 | 14:30:00 | | 42.34 | 34.19 | 10.70 | 92 |
| 10 | 15:00:00 | 58.00 | 40.98 | 32.08 | 10.68 | 92 |
| 11 | 15:30:00 | | 38.55 | 30.65 | 10.68 | 92 |
| 12 | 16:00:00 | 73.42 | 38.76 | 28.99 | 10.68 | 92 |
| 13 | 16:30:00 | | 38.11 | 26.90 | 10.58 | 92 |
| 14 | 17:00:00 | | 38.46 | 26.61 | 10.59 | 92 |
| 15 | 17:30:00 | | 38.75 | 26.31 | 10.59 | 92 |
| 16 | 18:00:00 | 84.77 | 38.78 | 24.56 | 10.59 | 92 |
| 17 | 19:00:00 | | 39.15 | 22.76 | 10.52 | 91 |
| 18 | 20:00:00 | | 36.87 | 20.54 | 10.52 | 91 |
| 19 | 22:00:00 | | 38.78 | 19.42 | 10.44 | 91 |
| 20 | 24:00:00 | 94.84 | 36.66 | 17.54 | 10.37 | 90 |
| 21 | 36:00:00 | 100.00 | 32.90 | 12.17 | 10.19 | 90 |
| 22 | 48:00:00 | | 33.26 | 9.81 | 10.04 | 91 |
| 23 | 60:00:00 | | | | 9.89 | 91 |

The results in Table 3 show that when ethylene diamine is added to the reaction mixture, it starts reacting with unreacted maleate present in the reaction mixture, whereas the formation of additional AES is essentially stopped.

The results also show that the content of EDDS increased to over 50% of the theoretical maximum already after 2-3 hours after the addition of ethylene diamine.

The results additionally show that after a reaction time of about 36 hours the yield of AES was about 33 mole % and the yield of EDDS was 100 mole % (based on the starting ethylene diamine).

2. Precipitation of Lanthanum Carbonate 138.53 g of the end product from the above synthesis was weighted into the starting flask. 80.36 g (0.227 moles) of $Na_2CO_3$ solution (aq. 30 wt %) was weighted into a precipitation vessel. The $Na_2CO_3$ concentration was about 2.5 times the concentration of lanthanum. The mixing was positioned at the bottom of the precipitation vessel. The speed and position were adjusted during the precipitation if the precipitate formed in the precipitation vessel was observed to form encased solution. A motor pump fed the reaction solution to be precipitated into the precipitation vessel containing the carbonate solution. The feeding speed was about 4 g per minute. The carbonate solution vessel was surrounded by a heating water housing. The pH of the carbonate solution was 11.34 and the temperature 60.3° C. The feeding time of the reaction mixture was about 1 hour. The rotation speed of the mixer was about 30 rpm. The mixing was continued after the end of the feeding of the solution for about 30 minutes whereafter the mixing and heating were stopped. The content of the precipitation vessel was allowed to settle until next day. A sample for particle size analysis of the precipitate was taken through the whole thickness of the solution-precipitate-phases from the bottom of the precipitation vessel up to the surface.

The precipitated reaction solution was filtrated by using a Büchner funnel, filter paper and suction. The obtained filtrate was a transparent solution. The filtrate was not rinsed. The lanthanum content was determined from the filtrated reaction solution by XRF and ICP-AES devices. The particle size was measured by a particle size analyzer (Malvern Instruments, Mastersizer 2000, Hydro SM small volume sample dispersion unit). The results from the particle size measurements are shown in enclosed FIG. 3.

Figure 3:
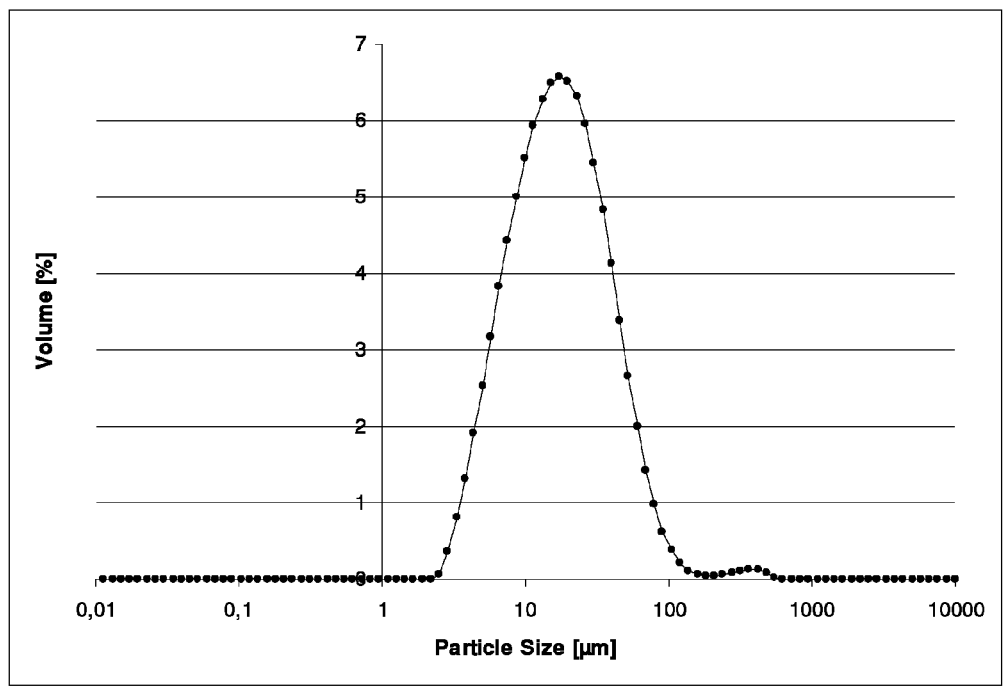
FIG. 3 shows the particle size distribution of lanthanum carbonate precipitate obtained according to the present invention.

The results in FIG. 3 show that 0.00% (volume) of the particles have a size of below 2 µm and the vol. weighted mean diameter is 11.08 µm. Example 1 shows that the presence of EDDS in the precipitation of lanthanum carbonate improves the quality of the precipitate such that the small fraction (<2 µm) is not at all present and the particle size distribution is very even.

Example 2

Precipitation of Lanthanum as Carbonate

1. Preparation of a Mixture of AES and ISA 98.06 g (1.000 mole) of maleic anhydride was dissolved in 258.40 g of water using a magnetic stirrer and heating to about 70° C. The aqueous maleic acid solution was transferred into a three-neck flask in a preheated oil bath. 148.70 g (0.263 moles) of $La_2(CO_3)_3$ precipitate was added as an aqueous slurry to the maleic acid solution. The addition was made slowly during about 5 minutes for controlling the effervescence caused by carbon dioxide. The pH before the addition of diethanol amine was 2.28 (T=71° C.). 31.14 g (0.252 moles) of diethanol amine was added into the reaction mixture. The addition of diethanol amine into the mixture raised the pH to 4.08 (T=73° C.). The temperature of the mixture was raised to about 90° C. The pH of the reaction solution was adjusted by adding 77.61 g (0.931 moles) of NaOH solution (aq. 48 wt %). The alkalinity of the reaction mixture was adjusted in connection with the second sample by adding 4.47 g (0.054 moles) of NaOH solution (aq. 48 wt %) to raise the pH to 8.55, and in connection with the third sample by adding 7.35 g (0.088 moles) of NaOH solution (aq. 48 wt %) to raise the pH to 9.16.

After 12 hours from the start of the measurements 61.71 g (0.459 moles) of DL-aspartic acid was added and the pH of the reaction mixture decreased to 5.60 (T=85° C.). The alkalinity was restored by adding 74.00 g (0.888 moles) of NaOH solution (aq. 48% by weight) and the pH raised to 9.98 (T=93° C.). After the addition of aspartic acid and alkali monitoring samples were taken with an interval of half an hour during six hours. Thereafter the sampling interval was extended. The reason for that was the fast synthesis of ISA from aspartic acid and maleate especially in the catalyzed reaction. At each occasion two samples were taken. Into one of the samples warm 30% by weight $Na_2CO_3$ solution was added immediately to stop the reaction catalyzed by lanthanum at the sampling moment. The other sample was stored and frozen. The analyses were taken from the samples treated with the carbonate solution. During the synthesis samples were taken at 23 moments. The total duration of the synthesis was 60 hours of which the 12 first were pure synthesis of AES.

More accurate information regarding the conditions and concentrations of the reaction mixture are set forth in following table 4.

TABLE 4

| Sample | Reaction time (hh:mm:ss) | ISA (mole %) | AES (mole %) | Maleic acid (%) | pH | T °C. |
|---|---|---|---|---|---|---|
| 1 | 0:00:00 | | 2.69 | 100.00 | 8.13 | 97 |
| 2 | 4:00:00 | | 5.64 | 92.37 | 8.26 | 90 |
| 3 | 8:00:00 | | 18.03 | 78.90 | 8.42 | 92 |
| 4 | 12:15:00 | | 37.14 | 69.90 | 9.53 | 93 |
| 5 | 12:35:00 | 2.15 | 34.38 | 62.82 | 9.98 | 93 |
| 6 | 13:05:00 | 6.88 | 34.04 | 59.04 | 9.98 | 92 |
| 7 | 13:35:00 | 10.72 | 36.13 | 57.41 | 9.98 | 91 |
| 8 | 14:05:00 | 13.15 | 37.12 | 57.13 | 10.06 | 91 |
| 9 | 14:35:00 | 18.56 | 38.80 | 55.98 | 10.05 | 91 |
| 10 | 15:05:00 | 19.78 | 35.79 | 48.51 | 10.07 | 91 |
| 11 | 15:35:00 | 22.58 | 38.15 | 51.42 | 10.12 | 91 |
| 12 | 16:05:00 | 24.99 | 36.29 | 50.36 | 10.17 | 91 |
| 13 | 16:35:00 | 27.48 | 36.42 | 47.06 | 10.12 | 91 |
| 14 | 17:05:00 | 29.53 | 36.29 | 46.20 | 10.10 | 91 |
| 15 | 17:35:00 | 31.47 | 37.06 | 45.67 | 10.09 | 91 |
| 16 | 18:05:00 | 33.52 | 36.15 | 43.90 | 10.12 | 91 |
| 17 | 19:05:00 | 37.02 | 36.21 | 41.27 | 10.06 | 92 |
| 18 | 20:05:00 | 40.20 | 36.22 | 40.72 | 10.13 | 93 |
| 19 | 22:05:00 | 45.93 | 36.16 | 37.64 | 10.15 | 92 |
| 20 | 24:05:00 | 50.59 | 34.84 | 35.48 | 10.15 | 91 |
| 21 | 36:05:00 | 67.78 | 33.19 | 24.15 | 10.21 | 92 |
| 22 | 48:05:00 | 75.90 | 31.62 | 18.13 | 10.07 | 93 |
| 23 | 60:05:00 | | | | 10.16 | 92 |

The results in Table 4 show that when aspartic acid is added to the reaction mixture, it stats reacting with unreacted maleate present in the reaction mixture, whereas the formation of additional AES is essentially stopped.

The results additionally show that after a reaction time of about 24 hours the yield of AES was about 35 mole % and the yield of ISA was about 50 mole % (based on the starting aspartic acid).

2. Precipitation of Lanthanum Carbonate 238.96 g of the end product from the above synthesis was weighted into the starting flask. 110.30 g (0.312 moles) of $Na_2CO_3$ solution (aq. 30 wt %) was weighted into a precipitation vessel. The $Na_2CO_3$ concentration was about 2.5 times the concentration of lanthanum. The mixing was positioned at the bottom of the precipitation vessel. The speed and position were adjusted during the precipitation if the precipitate formed in the precipitation vessel was observed to form encased solution. A motor pump fed the reaction solution to be precipitated into the precipitation vessel containing the carbonate solution. The feeding speed was about 3.5 g per minute. The carbonate solution vessel was surrounded by a heating water housing. The pH of the carbonate solution was 11.24 and the temperature 68.5° C. The feeding time of the reaction mixture was somewhat above 1 hour. The rotation speed of the mixer was about 30 rpm. The mixing was continued after the end of the feeding of the solution for about 30 minutes whereafter the mixing and heating were stopped. The content of the precipitation vessel was allowed to settle until next day. A sample for particle size analysis of the precipitate was taken through the whole thickness of the solution-precipitate-phases from the bottom of the precipitation vessel up to the surface.

The precipitated reaction solution was filtrated by using a Büchner funnel, filter paper and suction. The obtained filtrate was a transparent solution. The filtrate was not rinsed. The lanthanum content was determined from the filtrated reaction solution by XRF and ICP-AES devices. The particle size was measured by a particle size analyzer (Malvern Instruments, Mastersizer 2000, Hydro SM small volume sample dispersion unit). The results from the particle size measurements are shown in enclosed FIG. 4.

Figure 4:
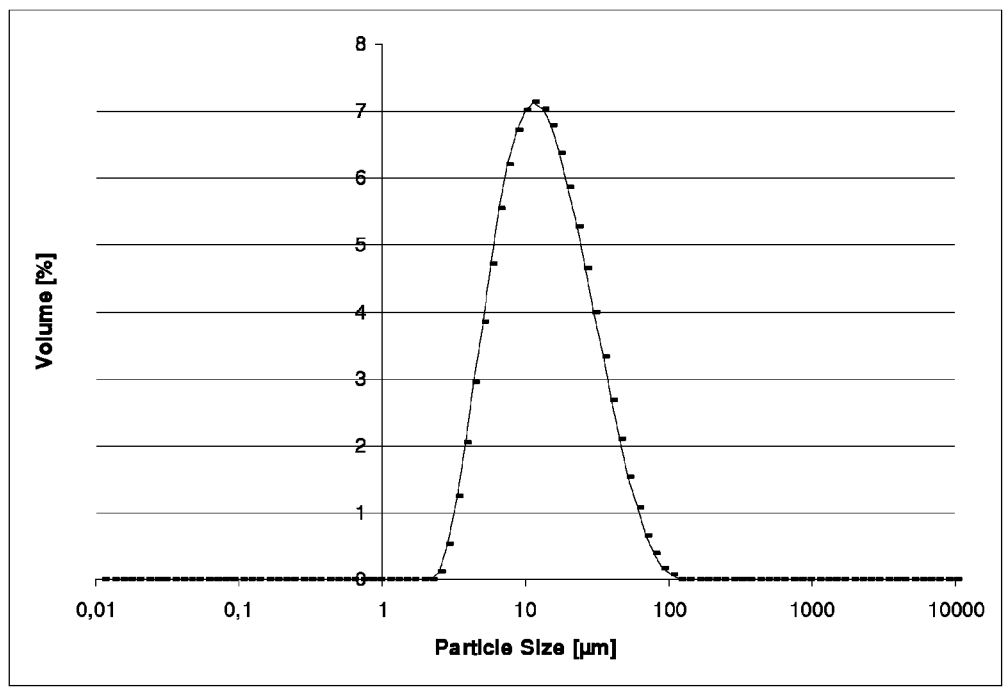
FIG. 4 shows the particle size distribution of lanthanum carbonate precipitate obtained according to the present invention.

The results in FIG. 4 show that 0.00% (volume) of the particles have a size of below 2 μm and the vol. weighted mean diameter is 9.71 μm. Example 2 shows that the presence of ISA in the precipitation of lanthanum carbonate improves the quality of the precipitate such that the small fraction (<2 μm) is not at all present and the particle size distribution is very even.

The invention claimed is:

1. A method for recovering lanthanoid catalyst from the preparation of aspartic acid diethoxy succinate comprising contacting a carbonate source with a solution containing lanthanoid ions derived from said preparation and a chelating agent different from aspartic acid diethoxy succinate to precipitate lanthanoid carbonate followed by separating the precipitated lanthanoid carbonate from the solution, wherein said chelating agent is imino disuccinic acid or ethylene diamine disuccinic acid.

2. The method according to claim 1 wherein the carbonate source is an alkali metal carbonate or alkaline earth metal carbonate or carbon dioxide.

3. The method according to claim 1 wherein the aspartic acid diethoxy succinate is prepared by reacting diethanol amine with maleate under alkaline conditions in the presence of the lanthanoid catalyst, and wherein the imino disuccinic acid is formed in situ by adding aspartic acid into the reaction mixture where it reacts with unreacted maleate to form imino disuccinic acid.

4. The method according to claim 1 wherein the aspartic acid diethoxy succinate is prepared by reacting diethanol amine with maleate under alkaline conditions in the presence of the lanthanoid catalyst, and wherein the imino disuccinic acid is formed in situ by adding aspartic acid into the reaction mixture where it reacts with unreacted maleate to form imino disuccinic acid.

5. The method according to claim 1 wherein the precipitated lanthanoid carbonate is separated by filtration.

6. The method according to claim 1 wherein the separated lanthanoid carbonate precipitate contains less than 5% by volume of particles having a particle size of less than 1 μm.

7. The method according to claim 1 wherein the lanthanoid catalyst is lanthanum catalyst and the lantanoid carbonate is lanthanum carbonate.

8. A process for the preparation of aspartic acid diethoxy succinate comprising reacting diethanol amine with maleate under alkaline conditions in the presence of a lanthanoid catalyst to form aspartic acid diethoxy succinate, said lanthanoid catalyst being precipitated from the reaction mixture by contacting the lanthanoid catalyst with a carbonate source and a chelating agent to form lanthanoid carbonate precipitate which is separated and reused as such as a lanthanoid catalyst in said process or converted into another lanthanoid catalyst to be used as a lanthanoid catalyst in said process, said chelating agent being different from aspartic acid diethoxy succinate, wherein said chelating agent is imino disuccinic acid or ethylene diamine disuccinic acid.

9. The process according to claim 8 wherein the carbonate source is an alkali metal carbonate or alkaline earth metal carbonate or carbon dioxide.

10. The process according to claim 9 wherein the precipitated lanthanoid carbonate is separated by filtration.

11. The process according to claim 8 wherein the separated lanthanoid carbonate precipitate contains less than 5% by volume of particles having a particle size of less than 1 μm.

12. The process according to claim 8 wherein the lanthanoid catalyst is lanthanum catalyst and the lantanoid carbonate is lanthanum carbonate.

13. The method according to claim 1 wherein the carbonate source is sodium carbonate.

14. The method according to claim 1 wherein the separated lanthanoid carbonate precipitate contains less than 3% by volume of particles having a particle size of less than 1 μm.

15. The method according to claim 1 wherein the separated lanthanoid carbonate precipitate contains less than 5% by volume of particles having a particle size of less than 2 μm.

16. The method according to claim 1 wherein the separated lanthanoid carbonate precipitate contains less than 3% by volume of particles having a particle size of less than 2 μm.

17. The process according to claim 8 wherein the carbonate source is sodium carbonate.

18. The process according to claim 8 wherein the separated lanthanoid carbonate precipitate contains less than 3% by volume of particles having a particle size of less than 1 μm.

19. The process according to claim 8 wherein the separated lanthanoid carbonate precipitate contains less than 5% by volume of particles having a particle size of less than 2 μm.

20. The process according to claim 8 wherein the separated lanthanoid carbonate precipitate contains less than 3% by volume of particles having a particle size of less than 2 μm.

* * * * *